(12) United States Patent
Nadeau et al.

(10) Patent No.: US 7,364,881 B1
(45) Date of Patent: Apr. 29, 2008

(54) BIOLOGICAL PROCESS FOR THE CONVERSION OF NITROARENES TO ORTHO-AMINOPHENOLS USING RECOMBINANT E. COLI STRAINS

(75) Inventors: Lloyd J. Nadeau, Callaway, FL (US); Jim C. Spain, Atlanta, GA (US); Venkateswarlu Kadiyala, Anantapur (IN)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 387 days.

(21) Appl. No.: 11/108,147

(22) Filed: Apr. 11, 2005

Related U.S. Application Data

(60) Provisional application No. 60/592,022, filed on Jul. 29, 2004.

(51) Int. Cl.
C12P 13/00 (2006.01)
C12N 1/20 (2006.01)
C07H 21/04 (2006.01)

(52) U.S. Cl. ............... 435/128; 435/170; 435/253.3; 435/193; 536/23.2

(58) Field of Classification Search ............... None
See application file for complete search history.

(56) References Cited

U.S. PATENT DOCUMENTS 6,797,497 B1  9/2004  Spain et al.

FOREIGN PATENT DOCUMENTS

GB  2302873 A  2/1997

OTHER PUBLICATIONS

Koder et al. ( protein expr. & purify. 1998, 13, 53-60).*
Davis et al. (Appld & environ Microbiol. 2000, 2965-2971).*
Nadeau et al. ( J. Inds. Microbiol & Biotech, 2000, 24, 301-305).*
Arechaga, I., B. Miroux, S. Karrasch, R. Huijbregts, B. Kruijff, M. J. Runswick, and J. E. Walker, 2000. Characterization of new intracellular membranes in Escherichia coli accompanying large scale over-production of the b subunit of $F_1F_0$ ATP synthase. FEBS letters 482:215-219.
Bryant, C., and M. DeLuca. 1991. Purification and characterization of an oxygen-insensitive NAD(P)H nitroreductase from Enterobacter cloacae. J. Biolog. Chem. 266:4119:4125.
Choe, E. W., and S. N. Kim, 1981. Synthesis, spinning, and fiber mechanical properties of poly (p-phenylenebenzoxazole). Macromolecules 14:920-924.
Davis, J. K., G. C. Paoli, Z. He, L. J. Nadeau, C. C. Somerville, and J. C. Spain, 2000. Sequence analysis and initial characterization of two isozymes of hydroxylaminobenzene mutase from Pseudomonas pseudoalcaligenes JS45. Appl. Environ. Microbiol. 66:2965-2971.
Dotrong, M., M. H. Dotrong, R. C. Evers, and G. J. Moore, 1990. One-step synthesis of high temperature 6F-polybenzoxazoles, Am. Chem. Soc.: Papers Pres. Am. Chem. Soc. Meet. 31:675-676.
Kadiyala, V., L.J. Nadeau, and J.C. Spain. 2003. Construction of E. coli strains for conversion of nitroacetophenones to ortho-aminophenols. Appl. Environ. Microbiol. 69:6520-6526.
Kadseda, H., T. Noguchi, and R. Kido. 1973. Biosynthetic routes to 2-aminoacetophenone and 2-amino-3-hydroxyacetophenone. J. Biochem. 74:127-133.
Koder, R. L., and A.-F. Miller. 1998. Overexpression, isotopic labelling, and spectral characterization of Enterobacter cloacaenitroreductase. Protein Expression Purification 13:53-60.
Nadeau, L. J., Z. He, and J. C. Spain. 2000. Production of 2-amino-5-phenoxyphenol from 4-nitrobiphenyl ether using nitrobenzene nitroreductase and hydroxylaminobenzene mutase from Pseudomonas pseudoalcaligenes strain JS45. J. Indust. Microbiol. Biotechnol. 24:301-305.
Nishino, S. F., and J. C. Spain. 1993. Degradation of nitrobenzene by a Pseudomonas pseudoalcaligenes. Appl. Environ. Microbiol. 59:2520-2525.
Somerville, C. C., S. F. Nishino, and J. C. Spain. 1995. Purification and characterization of nitrobenzene nitroreductase from Pseudomonas pseudoalcaligenes JS45. J. Bacteriol. 177:3837-3842.
Walker, J. E., and B. Miroux (ed.). 1999. Selection of Escherichia coli hosts that are optimized for the overexpression of proteins, 2nd ed. ASM Press, Washington, D.C.
Wolfe, J. F., and F. E. Arnold. 1981. Rigid-rod polymers. 1. Synthesis and thermal properties of para-aromatic polymers with 2,6-benzobisoxazole units in the main chain. Macromolecules 14:909-915.

* cited by examiner

Primary Examiner—Rebecca E. Prouty
Assistant Examiner—Younus Meah
(74) Attorney, Agent, or Firm—AFMCLO/JAZ; Bart S. Hersko

(57) ABSTRACT

A process for biological production of ortho-aminophenols from nitroaromatic compounds using recombinant E. Coli strains. The process uses an enzyme system that makes use of a nitroreductase enzyme that initially reduces the nitroarene to the hydroxylaminoarene and a mutase enzyme that converts the hydroxylaminoarene to an ortho-aminophenol.

5 Claims, 8 Drawing Sheets

Figure 1a Transformation of NB by whole cells of *E. coli* strain JS995
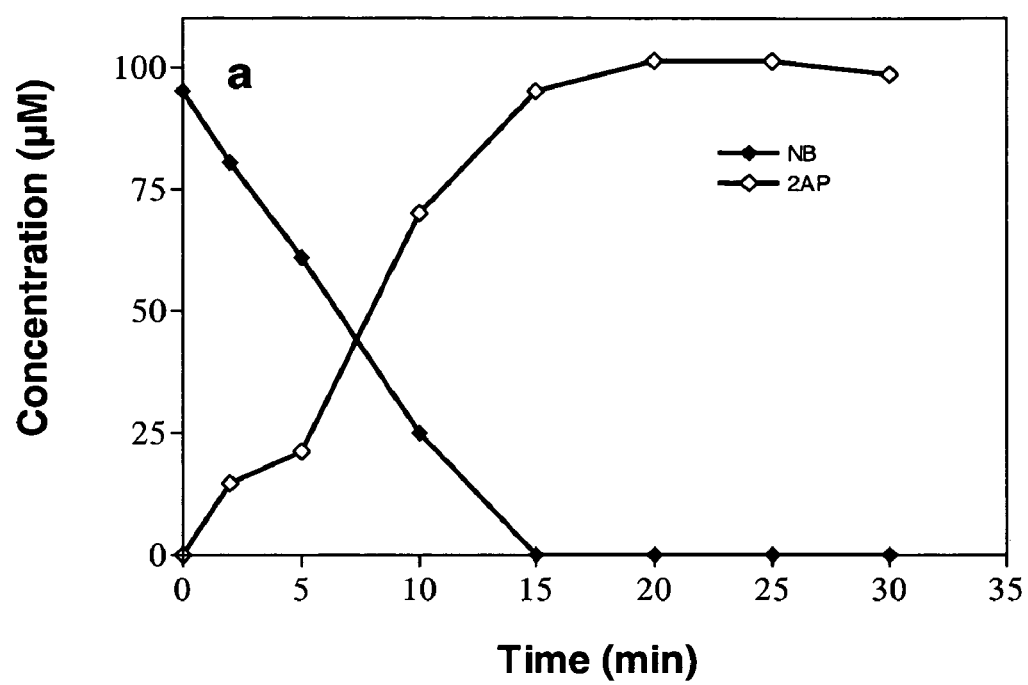

Figure 1b Transformation of NB by whole cells of *E. coli* strain JS996
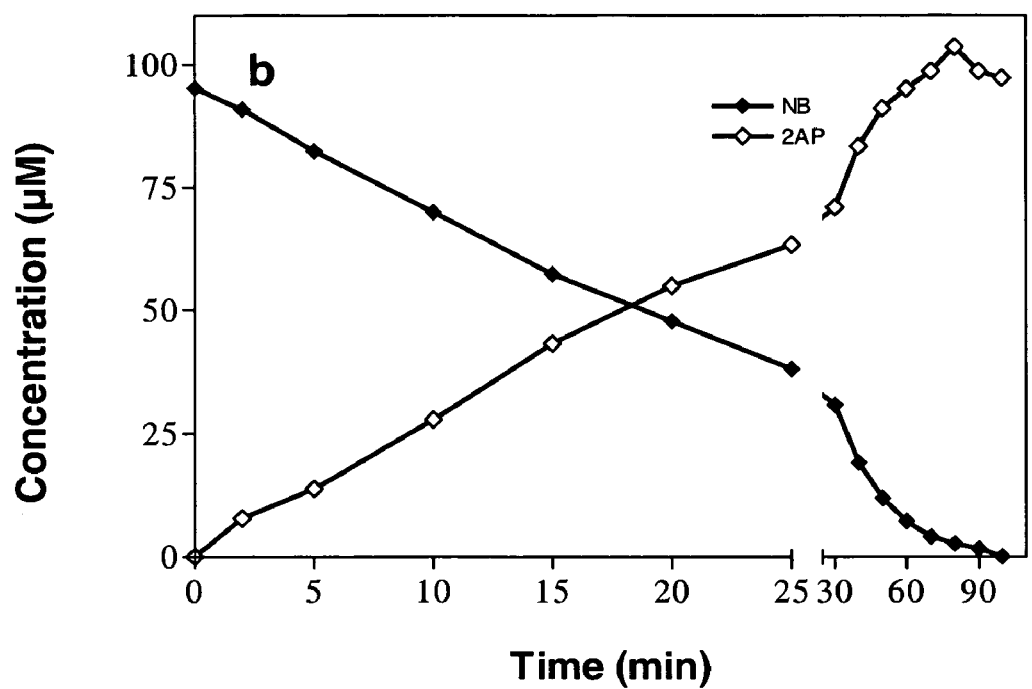

Figure 2a  Transformation of 2NAP by whole cells of strain JS995
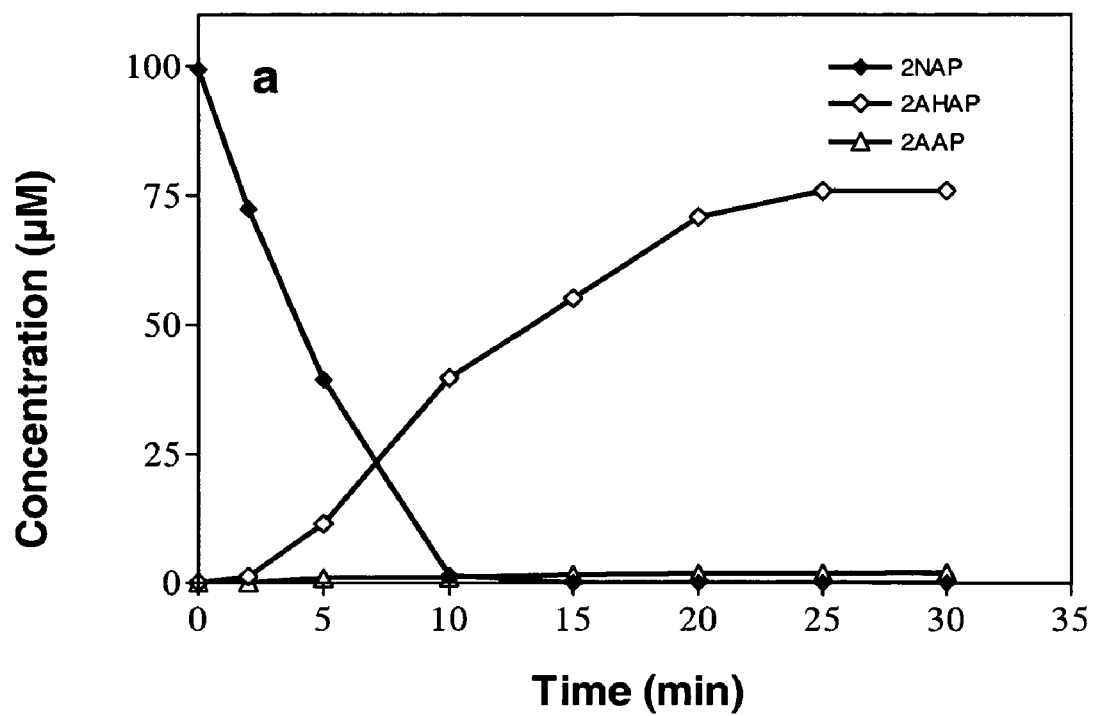

Figure 2b Transformation of 3NAP by whole cells of strain JS995
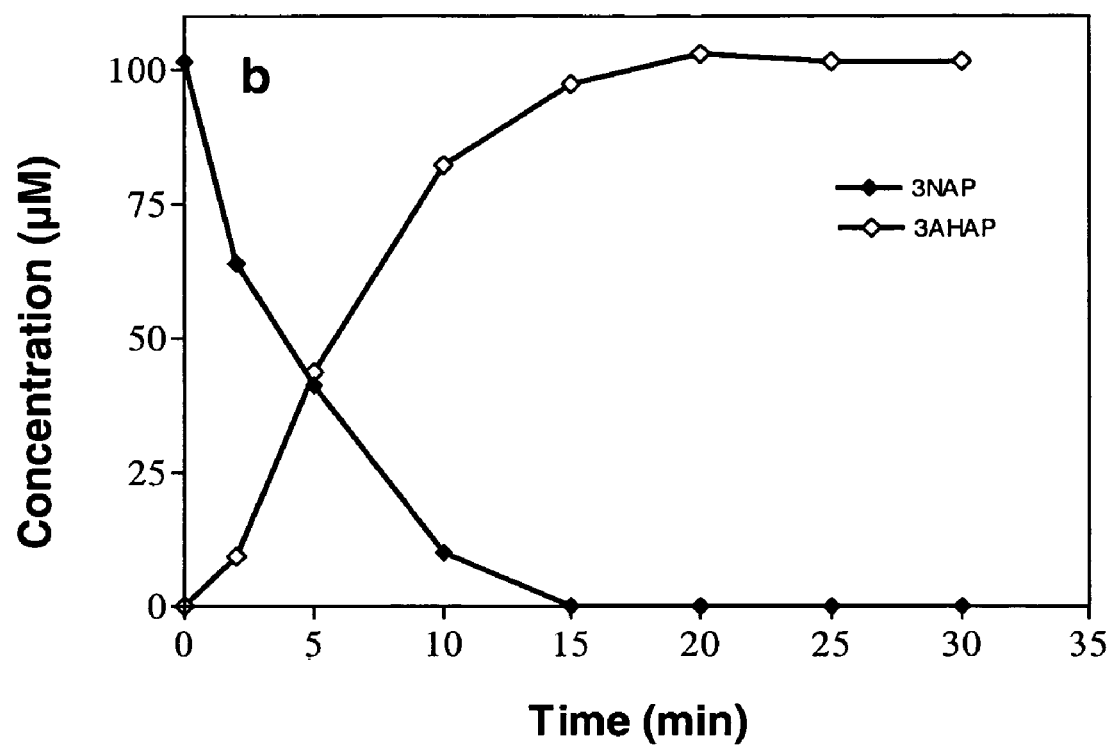

Figure 3a  Mass spectra of the end-product from 2NAP transformation by strain JS995
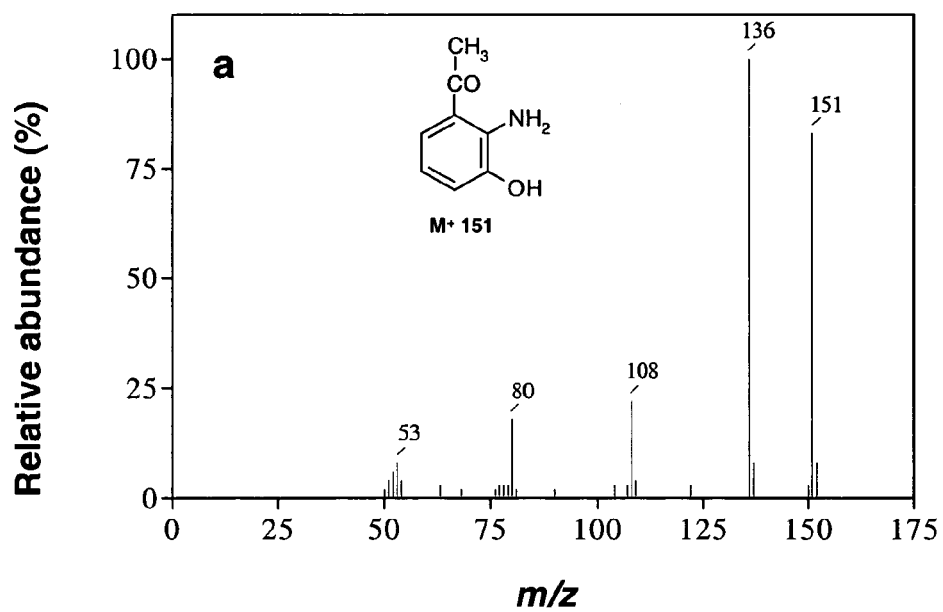

Figure 3b  Mass spectra of the n-butylboronic acid derivatized end-product from 2NAP transformation by strain
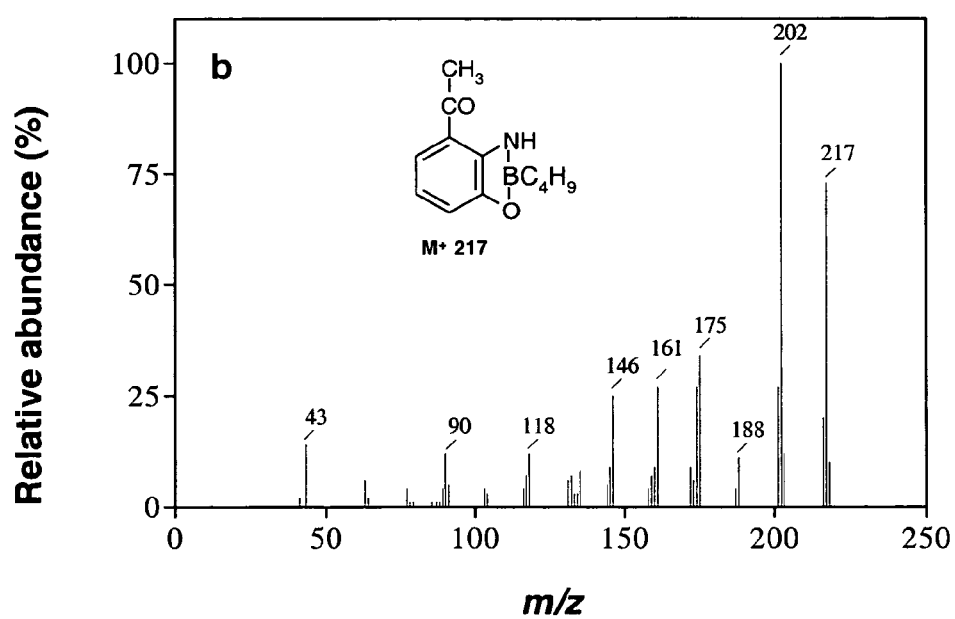

Figure 4a  Mass spectra of the end-product from 3NAP transformation by strain JS995
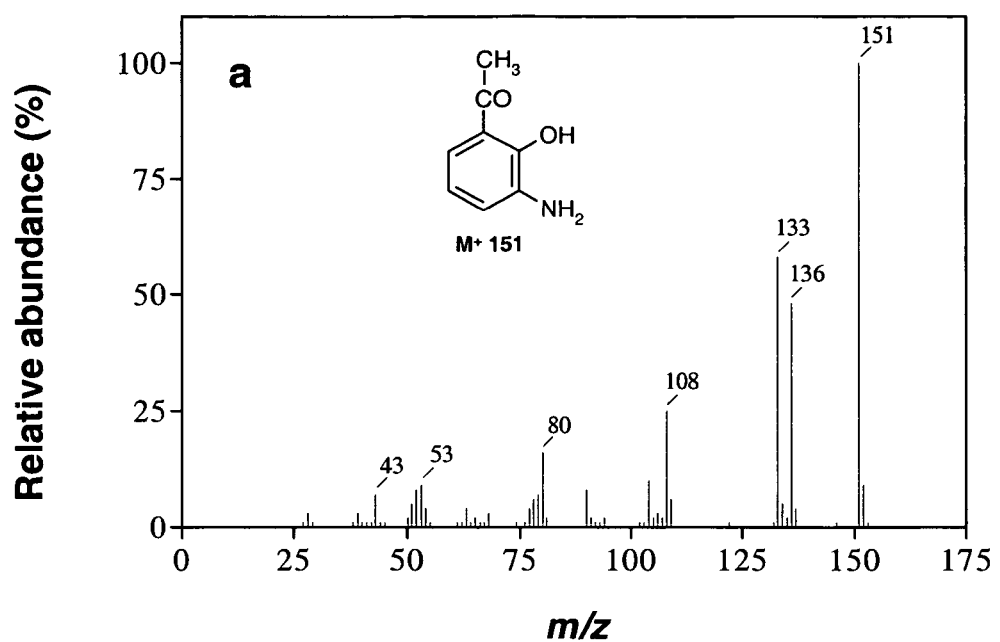

Figure 4b Mass spectra of the *n*-butylboronic acid derivatized end-product from 3NAP transformation by strain JS995
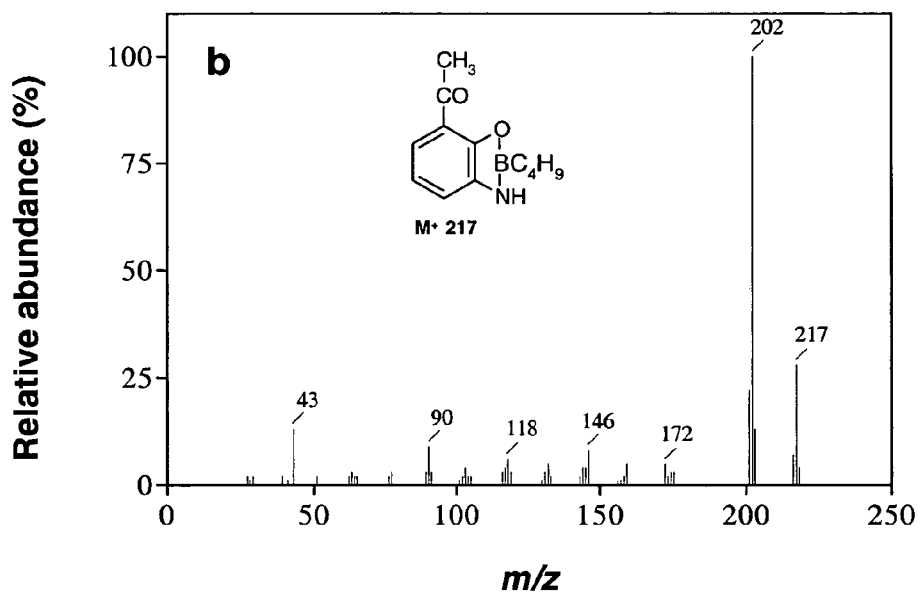

BIOLOGICAL PROCESS FOR THE CONVERSION OF NITROARENES TO ORTHO-AMINOPHENOLS USING RECOMBINANT E. COLI STRAINS

CROSS REFERENCE TO RELATED APPLICATION

This application claims priority of the filing date of Provisional Application Ser. No. 60/592,022, filed Jul. 29, 2004, the entire contents of which are incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates to the biological production of ortho-aminophenols from nitroaromatic compounds using recombinant bacteria.

Ortho-aminophenols are important building blocks for synthesis of polybenzoxazole polymers and biologically active compounds with potential aerospace applications. 2-Amino-3-hydroxyacetophenone (2AHAP) is an ortho-aminophenol of considerable biological and industrial significance. In particular, 2AHAP is an intermediate in oxidative metabolism of tryptophan in mammals and is a key monomer for the synthesis of 3-amino-4,5-diacetylphenoxazone, a dimer similar to the chromophore contained in actinomycin. A glucoside having excellent UV absorbing and scattering properties in the human lens is derived from 2AHAP and is potentially useful in the synthesis of a variety of compounds such as cosmetic humectants, antioxidants, and tyrosinase activity inhibitors. 2AHAP is a precursor for the synthesis of benzoxaprofen, a nonsteroidal antiinflammatory agent and also a possible precursor for the synthesis of acetal glucosides which are the allele chemicals in some plants. 3-Amino-2-hydroxyacetophenone (3AHAP) is a key feedstock for making 2-acetyl-6-[4-(4-phenylbutoxyl)benzoyl]aminophenol, an important pharmaceutical amide.

Because the above aminophenols are difficult to synthesize chemically and are consequently not commercially available, a biocatalytic synthesis of the compounds would be very useful.

In certain bacteria, the metabolism of nitroaromatic compounds occurs via the partial reduction of the nitro group to yield arylhydroxylamine intermediates which are subsequently converted to aminophenols or 1,2-dihydroxyl aromatic compounds. *Pseudomonas pseudoalcaligenes* JS45 grows on nitrobenzene (NB) as the sole carbon and nitrogen source by a partially reductive catabolic pathway. NB is reduced by NB nitroreductase to hydroxylaminobenzene (HAB), and HAB mutase then catalyzes the rearrangement of HAB to 2-aminophenol which serves as the substrate for meta-ring cleavage. Applicants previously showed that a combination of NB nitroreductase and HAB mutase from strain JS45 can catalyze the production of ortho-aminophenols from nitroaromatic compounds (see U.S. Pat. No. 6,797,497 incorporated herein by reference). In preliminary studies, partially purified NB nitroreductase and HAB mutase A from strain JS45 transformed 2NAP. The use of purified or immobilized enzymes is problematic, however, because the cofactor, NADPH, is consumed in the reaction. Furthermore, the presence of a ring-cleavage dioxygenase in NB-grown cells of JS45 or cell extracts limits its usefulness for the production of aminophenols.

Accordingly, it is an object of the present invention to provide an improved process for the biological production of ortho-aminophenols without the aforementioned problems.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided an improved process for the biological production of ortho-aminophenols from nitroaromatic compounds using recombinant *E. coli* strains. The process utilizes an enzyme system that makes use of a nitroreductase enzyme that initially reduces the nitroarene to the hydroxylaminoarene and a mutase enzyme that converts the hydroxylaminoarene to an ortho-aminophenol.

The reaction scheme can be represented as follows:

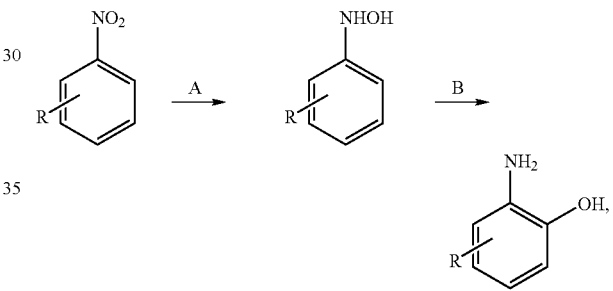

wherein R is selected from the group consisting of —H, —OH, —COOH, —$CnH_{2n+1}$, —$C_6H_5$, —X, —$CX_3$, —CHO, —$OC_nH_{2n+1}$, and —O—$C_6H_5$, wherein n ranges from 1 to 6, X is F, Cl, Br or I, A represents a nitroreductase and B represents the mutase enzyme. R can also consist of a fused ring as in nitronaphthalene or a heterocycle as in 4-nitro-N-methylphthalimide.

Examples of ortho-aminophenols that can be synthesized by the above process are selected from the group consisting of 2-aminophenol, 2-amino-3-methylphenol, 2-amino-4-methylphenol, 4-amino-5-phenoxyphenol, 2-amino-1-naphthol, 2-amino-3-hydroxy-acetophenone, 3-amino-2-hydroxy-acetophenone, 4-amino-5-hydroxy-N-methylphthalimide and mixtures thereof.

The listings of specific nitroaromatic compounds that can be used and/or synthesized in the enzyme system of the above process is intended to be merely exemplary in nature, and are not to be construed as limiting the scope of the present invention.

In particular, the improved process of the present invention comprises:

providing a recombinant *E. coli* strain that expresses both nitroreductase and mutase activities;

incubating said recombinant *E. coli* strain with a nitroarene; reducing said nitroarene to the corresponding hydroxylaminoarene by said nitroreductase;

converting said hydroxylaminoarene to said ortho-aminophenol by said mutase; and recovering a fraction containing said ortho-aminophenol.

In one embodiment, the *E. coli* is constructed from a recombinant plasmid carrying both NB nitroreductase and HAB mutase A genes. Preferably, both of the NB nitroreductase and the HAB mutase A genes are from *Pseudomonas pseudoalcaligenes*. Most preferably, the *Pseudomonas pseudoalcaligenes* strain is JS45 and the *E. coli* strain is JS995.

In another embodiment of the present invention, the *E. coli* strain is constructed from a recombinant plasmid carrying a NB nitroreductase gene (nfsl) from *Enterobacter cloacae* and a HAB mutase A gene from *Pseudomonas pseudoalcaligenes*. Preferably, the *Pseudomonas pseudoalcaligenes* strain is JS45 and the resultant *E. coli* strain is JS996.

BRIEF DESCRIPTION OF THE DRAWINGS

In the drawings:

FIG. 1a illustrates the transformation of nitrobenzene by whole cells of resultant *E. coli* strain JS995.

FIG. 1b illustrates the transformation of nitrobenzene by whole cells of *E. coli* strain JS996.

FIG. 2a illustrates the transformation of 2NAP by whole cells of strain JS995.

FIG. 2b illustrates the transformation of 3NAP by whole cells of strain JS995.

FIG. 3a illustrates the mass spectra of the end-product from 2NAP transformation by strain JS995.

FIG. 3b illustrates the mass spectra of the end-product from 2NAP transformation by strain JS995 derivatized with n-butylboronic acid.

FIG. 4a illustrates the mass spectra of the end-product from 3NAP transformation by strain JS995.

FIG. 4b illustrates the mass spectra of the end-product from 3NAP transformation by strain JS995 derivatized with n-butylboronic acid.

DETAILED DESCRIPTION OF THE INVENTION

The process of the present invention is a batch or continuous process in which whole cells of recombinant *E. coli* bacterial strains carrying genes for both the synthesis of a nitroreductase enzyme, hereinafter referred to as a reductase, and a mutase enzyme, hereinafter referred to as mutase, are used to convert a nitroarene to the corresponding ortho-aminophenol. The nitroarene is first transformed to a hydroxylaminoarene by the reductase, after which the mutase then catalyzes the transformation of the hydroxylaminoarene to the corresponding ortho-aminophenol.

In particular, Applicants constructed the strain encoding NB nitroreductase (nbzA) and HAB mutase A (habA) from JS45 using the pET-21a(+)/*E. coli* C43(DE3) expression system. Applicants also constructed a strain containing the nitroreductase (nfsl) gene from *Enterobacter cloacae* and habA from strain JS45 using the pSE380/*E. coli* JM109 expression system. The *E. cloacae* nitroreductase was chosen because it is also a member of a larger family of type I oxygen-insensitive nitroreductases, capable of reducing a variety of structurally diverse nitroaromatic compounds (Bryant, C., and M. DeLuca; "Purification and characterization of an oxygen-insensitive NAD(P)H nitroreductase from *Enterobacter cloacae*." J. Biolog. Chem. 1991, 266:4119-4125.)

Bacterial Strains, Plasmids, Culture Conditions and Chemicals

Examples of the bacterial strains and plasmids used in this invention are listed in Table 1. Cultures of *P. pseudoalcaligenes* JS45 were grown on NB as described in Nishino and Spain Degradation of nitrobenzene by a *Pseudomonas pseudoalcaligenes*." Appl. Environ. Microbiol. 1993, 59: 2520-2525, incorporated herein by reference.

*E. coli* strains were routinely grown in Luria-Bertani (LB) broth on horizontal shakers at 250 rpm and 37° C. *E. coli* BL21 (DE3) harboring pRKI expressing the nfsl gene from *E. cloacae*, provided by Anne-Frances Miller, was grown as described in Koder, R. L., and A.-F. Miller; "Overexpression, isotopic labeling, and spectral characterization of *Enterobacter cloacae* nitroreductase." Protein Expression Purification 1998, 13:53-60, incorporated herein by reference. During IPTG-induction, 2×TY (tryptone-yeast extract) medium was used for growing strain JS995 while strain JS996 was grown in 2×LB medium with 1% glycerol. When necessary, ampicillin at 100-200 μg ml$^{-1}$ was added to the medium. All the nitroaromatic compounds and 2-aminoacetophenone were purchased from Aldrich (Milwaukee, Wis.), and other chemicals were analytical grade.

TABLE 1

Bacterial strains and plasmids used in this invention

| Strain or Plasmid | Description | Reference or Source |
|---|---|---|
| *Escherichia coli* | | |
| C43(DE3) | Derivative of strain BL21(DE3) | 22 |
| JS995 | Strain C43(DE3) carrying recombinant plasmid pJS490 | This study |
| JM109 | F' {traD36 proAB+ lacI$^q$ lacZΔM15} endA1 recA1 hsdR17 (r$_k^-$, m$_k^+$) supE33 thi-1 gyrA96 relA1 Δ(lac-proAB) | Invitrogen |
| JS996 | Strain JM109 carrying recombinant plasmid pJS491 | This study |
| JS999 | Strain C43(DE3) carrying recombinant plasmid pJS489 | This study |
| Plasmids | | |
| pET-21a(+) | Expression vector, Ap$^r$ lacI$^q$ T7 promoter with multiple cloning sites | Novagen |
| pJS489 | pET-21a(+) containing nbzA from strain JS45 | This study |
| pJS490 | pET-21a(+) containing nbzA and habA from strain JS45 | This study |
| pRK1 | pET-24d(+) containing nfs1 from *Enterobacter cloacae* | 20 |
| pSE380::habA | pSE380 from Invitrogen containing habA from strain JS45 | 6 |
| pJS491 | pSE380 containing nfs1 from *E. cloacae* and habA from strain JS45 | This study |

Construction of the Strain JS995

PCR was used to amplify the nbzA gene (685 bp) from the strain JS45 genome (G. Zylstra, GenBank Accession Number AY664495). The forward primer 5'-CAGACATATGC-CGACCAGCCCGTTC-3' with an NdeI site (shown in italics), and the reverse primer 5'-GTGAGGATCCTGGTAATTGCTGAAACTA-3' containing a BamHI site (shown in italics) and a stop site (shown in boldface) were obtained from Integrated DNA Technology, Coralville, Iowa. PCR (25 cycles) conditions were as follows:

denaturation at 94° C. for 1 min, annealing at 55° C. for 1 min, and extension for 2 min at 72° C.; initial denaturation was for 3 min, and final elongation for 5 min. The PCR product was gel-purified, treated with NdeI and BamHI, then ligated into NdeI- and BamHI-digested pET-21a(+). The coding sequence of NB nitroreductase was thus joined to the initiation codon at the NdeI site of the vector. The resulting plasmid, designated pJS489, was transferred to *E. coli* JM109 to check for the presence of the insert, and subsequently into *E. coli* C43(DE3) for expression of nbzA.

The recombinant plasmid pSE380::habA was used as the template for PCR amplification of the habA gene (408 bp; GenBank accession no. AF028594). The primers used were 5'-CAGTCGAATTCAAGGAGATCACATTATG-3' (EcoRI site in italics, and ribosome-binding site and start site in boldface), and 5'-GATCAAGCTTACTAACGTAG-GATACCG-3' (HindIII site in italics and stop site in boldface). The gel-purified PCR product was double-digested with EcoRI and HindIII, and ligated with similarly treated pJS489. The resulting construct (pJS490) which couples nbzA and habA under control of the T7 promoter of pET-21a(+) was introduced into *E. coli* C43(DE3), and the strain was designated JS995.

Construction of the Strain JS996

The nfsI gene of *E. cloacae* was isolated from the recombinant plasmid, pRK1, using PCR with the primers 5'-ATTAGAGAATTCCAGGAGTTGTTATG-GATATCATTTCTGTCGC-3' (EcoRI site in italics, and ribosome-binding site and start site in boldface) and 5'-AT-TACCCGGGTCAGCACTCGGTCACAATCG-3' (XmaI site in italics and stop site in boldface). The amplicon (650 bp) and the recombinant plasmid pSE380::habA were cleaved with EcoRI and XmaI to allow subcloning of nfsI upstream from habA. The resulting plasmid (pJS491) was transferred to *E. coli* JM109, and the strain designated JS996.

Induction of the Recombinant Enzymes and Enzyme Activities in Cell Extracts

Cells of *E. coli* strains carrying the recombinant plasmids were grown at 37° C. in 250 ml of 2×TY medium or 2×LB with 1% glycerol containing 100 µg/ml ampicillin in an incubator shaker until the cultures reached an $A_{600}$ of 0.8. The cells were induced with 1 mM IPTG by incubating strain JS995 at 30° C. and strain JS996 at 37° C. with shaking for 16 h. The cells were harvested, washed twice in 20 mM potassium phosphate buffer, pH 8, and used directly in whole-cell transformation assays or for the preparation of cell extracts.

Cells were broken by two passages through a French pressure cell at 20,000 lb/in². The resulting lysate was centrifuged at 17,000×g for 20 min at 4° C., and the supernatant was used for enzyme assays. Reductase activity for various nitroaromatic compounds was determined spectrophotometrically by measuring the initial rate of NADPH disappearance. The activity of HAB mutase A was measured spectrophotometrically by monitoring the increase in absorbance at 283 nm, which indicates the formation of 2-aminophenol (2AP) from HAB.

Whole-Cell Biotransformations

Initially, IPTG-induced cells of strain JS996 were suspended to an $A_{6000}$f 2 in 20 mM potassium phosphate buffer (pH 7.0), and transformation of NB, 2-nitrotoluene, 3-nitrotoluene, 4-nitrobiphenyl ether and 1-nitronaphthalene was performed at 37° C. For comparison of the two strains in whole-cell biotransformations, induced cells were suspended to an $A_{600}$ of 0.75 in 25 ml of 50 mM potassium phosphate buffer, pH 8, with glucose 1% (w/v). The reaction was initiated by the addition of 100 µM NB to the cell suspension and incubation at 30° C. with shaking. Samples of the duplicate reaction mixtures were removed at intervals, added to equal volumes of acetonitrile on ice to stop the reaction, centrifuged at 13,000×g for 2 min, and analyzed by HPLC for product formation.

Transformation of nitroacetophenones by strain JS995 for isolation and purification of the corresponding aminophenols was carried out in 250 ml of 50 mM phosphate buffer, pH 8 containing 1% (w/v) glucose. Washed induced cells were suspended in the buffer to an $A_{600}$ of 6.8, and incubated at 30° C. with shaking. 2NAP or 3NAP (500 mM in ethanol) was added periodically over 2 h to provide a total of 120 mg of substrate. At the end of the incubation period, the cells were removed by centrifugation, and the pH of the supernatant was adjusted to 6.5. The solution was extracted with three 100 ml volumes of diethyl ether. The ether extracts were combined and concentrated to 30 ml under a stream of nitrogen. Aminophenols were back extracted with 50 ml of NaOH 5% (w/v) and the organic phase containing the amine was discarded. The pH of the aqueous phase was adjusted to 6.5, and the solution was extracted three times with 50 ml of diethyl ether. The ether extract was dried over sodium sulfate and concentrated to 5 ml under nitrogen. One milliliter of water was added and the product crystallized as the remaining ether was evaporated under nitrogen.

Analytical Methods

HPLC was performed on an Alltima Phenyl column (5 µm, 250 mm×4.6 mm; Alltech, Deerfield, Ill.) with an HP 1040M diode array detector (Hewlett-Packard, Wilmington, Del.) at a wavelength of 235 nm. The mobile phase was acetonitrile-13.5 mM trifluoroacetic acid (40:60 for 2NAP and its metabolites or 25:75 for 3NAP and its products) at a flow rate of 1.0 ml min$^{-1}$. Purified 2AHAP or 3AHAP was used to construct a linear calibration curve for quantification by HPLC. NB, 2-nitrotoluene, 3-nitrotoluene, 4-nitrobiphenyl ether and 1-nitronaphthalene, and the aminophenols formed were separated on a Supelcosil LC-ABZ+Plus column (250 by 4.6 mm from Supelco, Bellefonte, Pa.) using acetonitrile-water (50:50) at 1.0 ml min$^{-1}$.

2AHAP or 3AHAP and their N—O-bis(trimethylsilyl)-trifluoroacetamide (BSTFA; Alltech Associates, Inc., Deerfield, Ill.) or n-butylboronic acid derivatives were analyzed by gas chromatography-mass spectrometry (GC-MS) using an Agilent 5973 mass spectrometer (Agilent Technologies, Inc., Palo Alto, Calif.) and an Agilent Chemstation model 6890N gas chromatograph equipped with an HP-5 MS capillary column (30 m×0.25 mm×0.25 µm film thickness; Hewlett-Packard) as described in Nadeau, L. J., Z. He, and J. C. Spain; "Production of 2-amino-5-phenoxyphenol from 4-nitrobiphenyl ether using nitrobenzene nitroreductase and hydroxylaminobenzene mutase from *Pseudomonas pseudoalcaligenes* strain JS45." J. Indust. Microbiol. Biotechnol. 2000, 24:301-305, incorporated herein by reference. Helium was the carrier gas at a constant flow rate of 0.8 ml min$^{-1}$. The initial column temperature was 90° C. for 5 min, increased at 20° C. min$^{-1}$ to 280° C., and isothermal for 8 min. Protein concentrations were determined by the bicinchoninic acid assay using the BCA kit (Pierce, Rockford, Ill.) with bovine serum albumin as the standard.

The following examples illustrate the invention:

EXAMPLE 1

Expression of Reductases and Mutase with the Recombinant Systems

The activity of the nitroreductases towards the selected nitroaromatic compounds differed substantially between the two strains (Table 2). No nitroreductase activity toward NB or 2NAP was detected in extracts prepared from induced cells of the host strains carrying only the vectors. The specific activity of the recombinant NB nitroreductase expressed in strain JS995 with NB as the substrate was similar to that reported previously (2.4 U mg$^{-1}$ protein) in wild-type JS45. The NB nitroreductase in cell extracts of strain JS995 catalyzed rapid transformation (specific activity>1.1 U mg$^{-1}$ protein) of 13 out of 22 nitroaromatic compounds tested. Transformation rates did not seem to be affected by the position of the nitro group relative to the other substituent for the mononitro compounds. Both 1,3-dinitrobenzene (DNB) and 2,4,6-trinitrotoluene (TNT) were better substrates for NB nitroreductase than its physiological substrate. The specific activity of *E. cloacae* nitroreductase, expressed in strain JS996 was relatively low toward NB. It was very active, however, with TNT and DNB. The nitroreductase activity toward DNB and TNT in the control host strain containing vector alone was 0.10 and 0.30 U mg$^{-1}$ protein. Both nitroreductases reduce NB to the four-electron reduction product, HAB.

The specific activity of the HabA, which plays a physiological role in the degradation of NB by strain JS45, was markedly higher (7.5 U mg$^{-1}$ protein) in strain JS995 than in strain JS996 (0.3 U mg$^{-1}$ protein), wild-type JS45 (5.80 U mg$^{-1}$ protein) or strain HS 12 (1.5 U mg$^{-1}$ protein). The expression of HAB mutase A in strain JS995 is probably facilitated by the host's ability to produce a network of internal membranes in which the overexpressed membrane proteins accumulate. Similarly, using the host strain *E. coli* C43(DE3), Researchers have demonstrated the abundant over-production of subunit b of *E. coli* FiFo ATP synthase accompanied by the proliferation of intracellular membranes without formation of inclusion bodies. See, Arechaga, I., B. Miroux, S. Karrasch, R. Huijbregts, B. Kruijff, M. J. Runswick, and J. E. Walker; "Characterization of new intracellular membranes in *Escherichia coli* accompanying large scale over-production of the b subunit of $F_1F_0$ ATP synthase." FEES letters 2000, 482:215-219, incorporated herein by reference. Even though the expression levels of the enzymes in strain JS995 are higher than in strain JS996, there might be an advantage to its different substrate preferences of the nitroreductase in strain JS996.

TABLE 2

Specific activity[a] of recombinant nitroreductases in cell extracts of *E. coli* strains

| Substrate | NbzA[b] | Nfs1[c] |
|---|---|---|
| Nitrobenzene | 2.5 | 0.1 |
| 2-Nitroacetophenone | 1.6 | 0.1 |
| 3-Nitroacetophenone | 2.1 | 0.2 |
| 4-Nitroacetophenone | 1.7 | 0.9 |
| 2-Nitrobenzaldehyde | 2.3 | 0.7 |
| 3-Nitrobenzaldehyde | 2.0 | 0.3 |
| 4-Nitrobenzaldehyde | 0.1 | <0.1 |
| 2-Nitrobenzoic acid | 0.3 | <0.1 |
| 3-Nitrobenzoic acid | 0.3 | 0.1 |
| 4-Nitrobenzoic acid | 0.7 | 0.1 |
| 2-Nitrotoluene | 1.4 | <0.1 |
| 3-Nitrotoluene | 1.9 | 0.1 |
| 4-Nitrotoluene | 0.1 | <0.1 |
| 1,3-Dinitrobenzene | 2.9 | 5.1 |
| 4-Nitrobiphenyl ether | 0.8 | 0.2 |
| 2,4,6-Trinitrotoluene | 2.6 | 11.1 |

The values are averages of duplicates, and the deviation was <10%
[a]μmol of NADPH oxidized min$^{-1}$ mg$^{-1}$ protein
[b]*E. coli* JS995
[c]*E. coli* JS996

EXAMPLE 2

Biosynthesis of a Variety of Aminophenols Using Recombinant Strain JS996

Initially, to determine the potential of strain JS996 in the production of aminophenols, resting cell experiments were performed by incubating IPTG-induced cells with various nitroaromatic compounds. The rates of substrate transformation were 2.0, 0.47, 1.62, 1.13 and 0.93 nmol min$^{-1}$ mg$^{-1}$ protein for NB, 2-nitrotoluene, 3-nitrotoluene, 4-nitrobiphenyl ether and 1-nitronaphthalene, respectively, during the initial 10 min of reaction. The reaction products were 2-aminophenol, 2-amino-3-methylphenol, 2-amino-4-methylphenol, 4-amino-5-phenoxyphenol, and 2-amino-1-naphthol, respectively, and the corresponding conversion efficiencies at the end of 30 min incubation were 98.6, 27, 63.8, 100 and 53.6. The results suggest that the recombinant strain could be used to convert a variety of nitroaromatic compounds to the corresponding aminophenols.

EXAMPLE 3

Comparison of Recombinant Strains JS995 and JS996 with Respect to Nitrobenzene Conversion to 2-Aminophenol Strains JS995 and 996 were compared for their ability to produce 2AP from NB in a time-course experiment performed at 30° C. The conversion of NB was substantially faster in strain JS995 than in strain JS996 (FIG. 1). The specific activities for transformation of NB and production of 2AP during the initial 10 min of reaction with strain JS995 were 13.4 and 12.5 nmol min$^{-1}$ mg$^{-1}$ protein, while those with strain JS996 were 5.4 and 5.0 nmol min$^{-1}$ mg$^{-1}$ protein. The results taken with the data in Table 2 related to substrate range suggest that strain JS995 expressing nbzA and habA genes both derived from strain JS45 would be a more suitable biocatalyst for synthesis of ortho-aminophenols from the corresponding nitroaromatic compounds.

The transformation of NB by whole cells of *E. coli* strain JS995 is illustrated in FIG. 1*a*. Similarly, the transformation of NB by whole cells of *E. coli* strain JS996 is illustrated in FIG. 1*b*. In both FIGS. 1*a* and 1*b*, NB was added to a cell suspension ($A_{600}$ of 0.75) in 50 mM potassium phosphate buffer, pH 8.0, containing 1% glucose. The reaction mixture was monitored by HPLC for production of 2-aminophenol (2AP) from NB.

EXAMPLE 4

Biotransformation of Nitroacetophenones

When IPTG-induced cells of strain JS995 were incubated with 2NAP in the absence of glucose, the transformation rate was very low, and only 50 of the added substrate was transformed at the end of 110 min of incubation (data not shown). Under similar conditions, addition of glucose resulted in a rapid and extensive transformation of 2NAP yielding a single major product tentatively identified as 2AHAP. The specific activity for the transformation of 2NAP during the initial 10 min of reaction in the presence of glucose was 17.6 nmol min$^{-1}$ mg$^{-1}$ protein. The difference in specific activities between whole-cell assays and cell extracts of the constructed strain (Table 2) could be due to limitations in uptake of the substrate into the cells or availability of reducing equivalents in the whole-cell system. The results also indicate that a source for generating the required reduced cofactor for the initial reduction of 2NAP is necessary to support the transformation by whole cells.

The transformation of 2NAP by whole cells of *E. coli* strain JS995 is illustrated in FIG. 2*a*. Similarly, the transformation of 3NAP by whole cells of *E. coli* strain JS995 is illustrated in FIG. 2*b*. In both FIGS. 2*a* and 2*b*, substrate was added to a cell suspension ($A_{600}$ of 0.75) in 50 mM potassium phosphate buffer, pH 8.0, containing 1% glucose. Production of aminophenol or 2-aminoacetophenone (2AAP) from the nitroacetophenone was monitored by HPLC.

The reaction was carried out on a larger scale and the major product was extracted for rigorous identification. The light-brown crystals of 2AHAP had a melting temperature of 180-183° C.; the reported values are 185-187° C. The absorption maxima of 2AHAP in methanol were 232, 270 and 375 nm; the reported values are 233, 270 and 378 nm. Analysis of the product by GC-MS revealed a compound (Rt of 8.32 min) with a parent ion at m/z 151 consistent with the expected mass of 2AHAP and a base peak at 136, which indicates the loss of a $CH_3$ group (M-15) (see FIG. 3*a*). The other predominant ions at m/z 108 (M-43), 80 (M-71) and 53 (M-98) were consistent with losses of exocyclic CO, endocyclic CO, and CNH. The BSTFA-derivatized product (Rt 7.57 min) yielded a parent ion at m/z 223 and is consistent with derivatization of a single substituent of 2AHAP (data not shown). Both the amino and hydroxyl substituents can be derivatized by BSTFA but the hydroxyl group is more reactive. Other fragment ions at m/z 208 (M-15), 192 (M-31), 166 (M-57), 150 (M-73) and 73 (M-150) correspond to the loss of $CH_3$, $NH_2$, CN, $CH_3$ and $C_8H_8NO_2$, respectively. To verify the position of the substituents, the product was derivatized with n-butylboronic acid. The only product formed had a GCMS Rt of 8.96 min, with a parent ion at m/z 217 and a base peak at 202 (see FIG. 3*b*). The results clearly indicate the presence of vicinal functional groups with reactive protons and a structure consistent with rearrangement of a hydroxylamine to the corresponding aminophenol. Based upon mass spectra and NMR data (Table 3), the major product from 2NAP was identified conclusively as 2AHAP.

During larger-scale transformation by strain JS995, 3 mM 2NAP yielded 2.2 mM 2AHAP; thus the conversion efficiency of the reaction was 75%. The only other detectable product, accounting for <10% of the substrate transformed, was 2 MP. It was, however, not clear whether nonspecific reductases of *E. coli* or the NB nitroreductase and HAB mutase A in strain JS995 were responsible for the formation of 2AAP. During solvent extraction, 2AAP partitioned into the diethyl ether phase at a pH of 13.4, and thus could be separated from 2AHAP, which remained in the aqueous phase. The aminophenol was stable in neutral solution at 4° C. for more than 8 months.

By using several steps in a complex chemical process with 2-nitro-3-methoxyacetophenone as an intermediate, 2AHAP has been synthesized with a yield of less than 13%. (Kaseda, H., T. Noguchi, R. Kido, and Y. Matsumura; The isolation and identification of 2-amino-3-hydroxyacetophenone from urine of rats. Experientia 1970, 26:828-829.) However, a 96% yield of 2AHAP by catalytic hydrogenation of 3-hydroxy-2-nitroacetophenone, an intermediate synthesized initially by a chemical process has been reported. (Escobar, C. A., M. Kluge, and D. Sicker; Biomimetic synthesis of 4-acetylbenzoxazolin-2(3H)-one isolated from *Zea mays*. J. Heterocyclic Chem. 1997, 34:1407-1414.) The results presented here indicate that whole cells of strain JS995 catalyze the rapid conversion of 2NAP to 2AHAP in good yield and in a single reaction.

Strain JS995 also transformed 3NAP very rapidly to a single product tentatively identified as 3AHAP in stoichiometric amounts (FIG. 2*b*). A metabolite formed transiently (Rt 5.56 min) during the conversion of 3NAP and disappeared with the concomitant accumulation of 3AHAP. The intermediate is likely the hydroxylamino compound. The reaction was carried out on a larger scale and the product was extracted for detailed analysis. The melting point of the brown crystalline product was 185-187° C., and the absorption maxima in methanol were 231, 274 and 360 nm. The mass spectrum of the compound (Rt 7.19 min) revealed a parent ion at m/z 151, a base peak at 136 (M-15), and other fragment ions at m/z 133 (M-18), 108 (M-43), 80 (M-71) and 53 (M-98), corresponding to the loss of $H_2O$, exocyclic CO, endocyclic CO and CNH, respectively (see FIG. 4*a*). As with 2AHAP, derivatization of the product from 3NAP with n-butylboronic acid yielded a single compound with a gas chromatography Rt of 8.44 min, a parent ion at m/z 217 consistent with expected mass of the product derivatized at adjacent hydroxyl and amino groups, and a base peak at 202 (see FIG. 4*b*). The NMR analysis (DMSO-$d_6$) of the product formed from 3NAP revealed $^1$H nmr: δ 2.60 (s, 3H, $CH_3$), 6.70 (dd, 1H, $H_5$), 6.88 (dd, 1H, $H_4$), 7.12 (dd, 1H, H6), 4.99 (s, 1H, OH), 3.32 (s, 2H, NH and OH), and $^{13}$C nmr: δ 27.1 ($CH_3$), 119.6 (C-5), 133.1 (C-1), 119.6 (C-4), 118.8 (C-6), 162.7 (C-2), 149.5 (C-3) and 206.6 (CO). The results are consistent with the structure of 3AHAP.

A Japanese patent (KOKAI publication # 95144/1991) describes the chemical synthesis of 3AHAP from p-chlorophenol by a multi-step process involving acetylation followed by Fries rearrangement, nitration and catalytic reduction. Our results show that 3AHAP can be biosynthesized as a single product from 3NAP in good yields.

TABLE 3

$^{13}$C and $^1$H NMR data for the product of 2NAP

| δ (ppm) | $^{13}$C | | $^1$H | |
|---|---|---|---|---|
| Position | Reported[a] | Obtained | Reported[a] | Obtained |
| 1 | 116.9 | 116.9 | | |
| 2 | 140.9 | 141.9 | | |
| 3 | 144.8 | 145.4 | | |
| 4 | 117.4 | 117.6 | 6.85 (dd) | 6.86 (dd) |
| 5 | 114.0 | 114.7 | 6.43 (dd) | 6.43 (dd) |
| 6 | 122.6 | 123.7 | 7.26 (dd) | 7.20 (dd) |
| 7 (CO) | 200.5 | 200.8 | | |
| 8 ($CH_3$) | 28.3 | 28.2 | 2.50 (s) | 2.50 (s) |
| (NH, OH) | 6.71 (s) | 6.69 (s) | | |

[a]Escobar et al. (8)

Having thus described exemplary embodiments of the present invention, it should be noted by those skilled in the art that the disclosures herein are exemplary only and that alternatives, adaptations and modifications may be made within the scope of the present invention.

We claim:

1. A process for the production of ortho-aminophenols from nitroarenes, said process comprising:

a) providing a recombinant bacteria that expresses both nitroreductase and mutase activities, wherein said recombinant bacteria is an *E. coli* strain, and wherein said *E. coli* strain is JS995;

b) incubating said recombinant bacteria strain with a nitroarene;

c) reducing said nitroarene to the corresponding hydroxylaminoarene by said nitroreductase;

d) converting said hydroxylaminoarene to said ortho-aminophenol by said mutase; and e) recovering a fraction containing said ortho-aminophenol, wherein said ortho-aminophenol is selected from the group consisting of 2-aminophenol, 2-amino-3-methylphenol, 2-amino-4-methylphenol, 4-amino-3-hydroxybenzoate, 4-amino-5-phenoxyphenol, 2-aminonaphthol, 4-amino-3-hydroxy-α,α,α,-trifluorotoluene, 2-amino-3-hydroxyacetophenone, and 3-amino-2-hydroxyacetophenone.

2. The process of claim 1 wherein said nitroarene has the formula

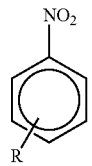

wherein R is selected from the group consisting of —H, [—CH$_3$]—CH$_3$, —COOH, —O—C$_6$H$_5$, —C$_6$H$_5$, —CX$_3$, and —COCH$_3$, wherein X is F, Cl, Br or I.

3. The process of claim 2 wherein said recombinant bacteria is constructed from a recombinant plasmid carrying both nitrobenzene nitroreductase and hydroxylaminobenzene mutase A genes.

4. The process of claim 3 wherein both said nitrobenzene nitroreductase and said hydroxylaminobenzene mutase A genes are from *Pseudomonas pseudoalcaligenes*.

5. The process of claim 4 wherein both said *Pseudomonas pseudoalcaligenes* strains are JS45.

* * * * *